United States Patent [19]

Krause et al.

[11] Patent Number: 5,821,385
[45] Date of Patent: Oct. 13, 1998

[54] PROCESS FOR THE PREPARATION OF N-(2-CARBOXY-5-CHLORO-PHENYL)GLYCINE

[75] Inventors: Stefan Krause, Sulzbach/Ts.; Doris Neumann-Grimm; Theodor Papenfuhs, both of Frankfurt, all of Germany

[73] Assignee: Hoechst Aktiengesellschaft, Frankfurt, Germany

[21] Appl. No.: 877,830

[22] Filed: Jun. 18, 1997

[30] Foreign Application Priority Data

Jun. 20, 1996 [DE] Germany .......................... 196 24 583.4

[51] Int. Cl.⁶ .................................................. C07C 229/00
[52] U.S. Cl. .............................................................. 562/456
[58] Field of Search ............................................. 562/456

[56] References Cited

FOREIGN PATENT DOCUMENTS 142507   6/1903   Germany .
97/08129  3/1997   WIPO .

OTHER PUBLICATIONS

Beilsteins Handbuch Der Organischen Chemie, 4 Auflage, 2, Ergänzungswerk Band 14, Springer–Verlag, Berlin Seite 231, Zeilen 6–16, 1951.
Beilsteins Handbuch Der Organischen Chemie, 4. Auflage, Band 14, Verlag von Julius Springer, Berlin Seite 366, Zeilen 17–22, 1931.
Beilsteins Handbuch Der Organischen Chemie, 4. Auflage, 4. Ergänzungswerk Band 14, Springer–Verlag, Berlin Seite 1074, Zeilen 14–19, 1985.

*Primary Examiner*—Gary Geist
*Assistant Examiner*—Brian J. Davis
*Attorney, Agent, or Firm*—Connolly & Hutz

[57] ABSTRACT

The present invention relates to a process for the preparation of N-(2-carboxy-5-chloro-phenyl)glycine of the formula (1)

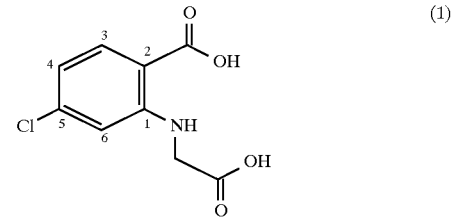

which comprises reacting 2,4-dichlorobenzoic acid of the formula (2)

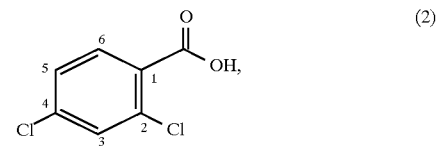

with glycine and a base in water at a temperature of 50° to 200° C. in the presence of copper and oxygen at a pH of 7 to 13.

22 Claims, No Drawings

PROCESS FOR THE PREPARATION OF N-(2-CARBOXY-5-CHLORO-PHENYL)GLYCINE

The present invention relates to a process for the preparation of N-(2-carboxy-5-chloro-phenyl)glycine which is improved compared with the prior art.

2-Carboxyphenylglycines are important, inter alia, for the industrial preparation of indigo. According to Ullmann's Encyclopedia of Industrial Chemistry, Vol. A. 14, pages 105 to 151, they can be prepared by reaction of anthranilic acid with chloroacetic acid. However, this type of synthesis presents problems, since the amino group in the anthranilic acid can react with the chloroacetic acid not only once but also twice, and thus leads to the formation of dialkylated products.

6,6'-Dichloroindigo is accessible starting from N-(2-carboxy-5-chloro-phenyl)glycine. It is known that the substituents on the indigo matrix have an influence on the absorption maxima of the indigo. Thus, as can be seen from H. Zollinger, Color chemistry: syntheses, properties and applications of organic dyes and pigments, VCH Verlagsgesellschaft Weinheim—New York 1987, pages 152 to 159, 6,6'-dichloroindigo has an absorption maximum for the longest wavelength at 590 nm (see also Table 8-1 on page 154).

Another synthesis, which is also described in Ullmann's Encyclopedia, comprises reacting anthranilic acid with formaldehyde and hydrogen cyanide. However, the use of highly toxic hydrogen cyanide (hydrocyanic acid) is a disadvantage of this preparation.

DE-C 142 507 relates to the preparation of phenylglycine-o-carboxylic acid (2-carboxyphenylglycine) by reaction of the potassium salt of 2-chlorobenzoic acid with glycine in the presence of potassium hydroxide, potassium carbonate and catalytic amounts of copper. In this procedure, all the reaction components are first of all initially introduced into the reaction vessel as a solution in water and are then heated up. However, difficulties result when carrying out this reaction using 2,4-dichlorobenzoic acid. On the one hand, by-products are formed in relatively large amounts, and, on the other hand, the reaction does not lead to reproducible results, since the reaction often does not proceed to completion but, without a detectable reason, leads only to a comparatively low partial conversion and then stops.

In view of the disadvantages described above, there is a need for a process which avoids the disadvantages described above and furthermore can be realized easily and without great industrial expenditure. The process should produce the desired product in high yields and furthermore should be reliably reproducible.

This object is achieved by a process for the preparation of N-(2-carboxy-5-chloro-phenyl)glycine of the formula (1)

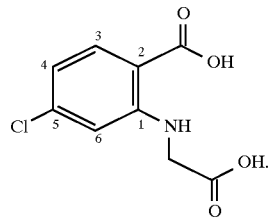

(1)

It comprises reacting 2,4-dichlorobenzoic acid of the formula (2)

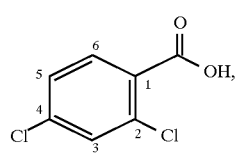

(2)

with glycine and a base in water at a temperature of 50° to 200° C. in the presence of copper and oxygen at a pH of 7 to 13.

The process according to the invention has several advantages. On the one hand, it starts from starting substances which are comparatively easily accessible, and can be carried out in a simple manner. Furthermore, it produces the desired N-(2-carboxy-5-chloro-phenyl)glycine in high to very high yields, based on the starting substances employed. It is ensured here that the process always leads to reproducible results in respect of conversion, selectivity and therefore yield, and it is not left to chance whether and to what extent the reaction proceeds to the desired product.

Chemical processes are as a rule carried out with exclusion of oxygen or air respectively. This particularly applies in the realization of chemical syntheses on industrial scales. If such a procedure is applied to the preparation of N-(2-carboxy-5-chloro-phenyl)glycine and the reaction of 2,4-dichlorobenzoic acid of the formula (2) with glycine and a base is carried out in water with exclusion of oxygen or air respectively, the reaction progresses only up to a certain degree of conversion, and then stops. Although starting substances which have not yet reacted are present, and although the reaction conditions are maintained unchanged, the reaction cannot be continued further—as a corresponding comparison experiment demonstrates—30 and the yield of the desired N-(2-carboxy-5-chloro-phenyl)glycines cannot be increased further.

The same behavior can be observed if the reactants are introduced into the reaction vessel, for example into a glass flask, and the reaction is carried out in the presence of the air still present in the reaction vessel. Here also — as comparison experiments show — the reaction proceeds in a non-reproducible manner up to a certain degree and then also stops.

However, in both the cases described above, the reaction can unexpectedly be conducted further if oxygen or air respectively is fed to the reaction and the reaction is thus continued in the presence of oxygen or air respectively. These properties indicate that only the presence of a sufficient amount of oxygen or air respectively during the entire reaction ensures that the reaction proceeds to the desired extent and in a reproducible manner. This was in no way to be predicted, and it is to be regarded as very surprising that the presence of oxygen evidently favorably influences the reaction.

If 2,4-dichlorobenzoic acid is reacted with glycine analogously to DE-C 142 507 by initially introducing all the reactants into the reaction vessel and then carrying out the reaction while stirring and heating, by-products, in particular 4-chlorosalicylic acid, form - as a corresponding comparison experiment demonstrates - to a not inconsiderable extent. The statement made in DE-C 142 507, that the yield is almost the yield in theory when 2-chlorobenzoic acid is used, cannot be confirmed if 2,4-dichlorobenzoic acid is used as the starting substance.

The formation of by-products, in particular 4-chlorosalicylic acid, can surprisingly be reduced significantly, however, by carrying out the reaction at a certain pH, as stated above. This can be realized particularly easily if the base is fed to the reaction in an amount such that the desired pH is maintained.

For carrying out the process according to the invention, it is necessary to carry out the reaction of the 2,4-dichlorobenzoic acid of the formula (2) with glycine in water both in the presence of oxygen and at the abovementioned pH. These two measures are to be adhered to in order to ensure the desired success.

It is not necessary to follow any particular sequence in respect of addition of the reaction partners; it is merely to be ensured that all the reactants which participate in the reaction are present during the reaction.

Only if carbonates are used as a mixture with hydroxides should the carbonates be added last.

The 2,4-dichlorobenzoic acid of the formula (2), glycine and water are usually initially introduced into the reaction vessel, and some of the base is then added, in order to form the corresponding salts from the 2,4-dichlorobenzoic acid and the glycine. The copper required as a catalyst for the reaction can be added beforehand or else afterwards.

The water serves as a solvent both for the 2,4-dichlorobenzoic acid, glycine and salts thereof and for the N-(2-carboxy-5-chloro-phenyl)glycine, which is obtained in the form of salts. Water is added in an amount such that the abovementioned substances dissolve therein completely or partly, and furthermore a solution or a suspension of not too high a viscosity is formed, in order to ensure good stirrability of the reaction mixture.

The water to 2,4-dichlorobenzoic acid weight ratio usually used is (0.5 to 10):1, in particular (0.7 to 5):1, preferably (1 to 3):1. Larger amounts of water, for example up to 15:1 or 20:1, can also be used, but relatively large volumes of aqueous solutions which must be handled are obtained by this procedure.

It is also possible, however, to use the corresponding salts of 2,4-dichlorobenzoic acid and of glycine directly and to dissolve these in water. In this case also, it is necessary to make available a sufficient amount of water so that the salts of 2,4-dichlorobenzoic acid and those of glycine dissolve completely or partly and a solution or suspension of not too high a viscosity is formed.

The reactants required for the reaction can be reacted in a wide molar ratio. The 2,4-dichlorobenzoic acid of the formula (2) and glycine are usually reacted in a molar ratio of 1:1 to 1:2, in particular 1:1 to 1:1.5.

All substances which have an adequate basicity can be used as the base. An oxide, hydroxide, carbonate or bicarbonate of an alkali metal or alkaline earth metal or a mixture thereof, in particular an oxide, hydroxide or carbonate of an alkali metal or a mixture thereof, preferably sodium hydroxide, potassium hydroxide, sodium carbonate or potassium carbonate or a mixture thereof, can be employed as the base with good success. A mixture comprising sodium hydroxide/sodium carbonate and/or potassium hydroxide/potassium carbonate is particularly preferred.

As already mentioned, the reaction can be carried out in a temperature range from 50° to 200° C.

In a large number of cases it is sufficient to carry out the reaction at a temperature of 60 to 160, in particular 90° to 130° C.

Copper is required as the catalyst for carrying out the reaction.

Metallic copper, for example in the form of filings, powder or copper bronze, a copper(I) or copper(II) compound or a mixture thereof, in particular a copper(I) salt or a copper(II) salt or a mixture thereof, can be employed as the copper.

Copper(I) and copper(II) compounds which may be mentioned, without claim to completeness, are copper(I) chloride, copper(II) chloride, basic copper carbonate, copper (I) oxide, copper(II) oxide, copper carbonate, copper(II) nitrate, copper(II) sulfate, copper acetate and copper acetylacetonate.

For carrying out the process, it is sufficient in most cases to add 0.005 to 2.5, in particular 0.02 to 1.5, preferably 0.05 to 0.5 % by weight of copper (calculated as elemental or chemically bonded copper), based on the 2,4-dichlorobenzoic acid, to the reaction. However, it is also possible to allow the reaction to proceed in the presence of larger amounts of copper, for example up to 4 or 5% by weight, based on the 2,4-dichlorobenzoic acid of the formula (2). However, such high amounts of copper as a rule lead to no particular advantage.

As explained above, the process according to the invention requires the presence of oxygen. Pure oxygen or an oxygen-containing gas is employed as the oxygen. It is merely to be ensured here that the oxygen is made available in a sufficient amount. This can be ensured particularly easily by passing pure oxygen or an oxygen-containing gas through the reaction mixture during the reaction. Air is usually employed as the oxygen-containing gas.

The process according to the invention can usually be carried out in a comparatively wide pH range, that is to say at a pH of 7 to 13. However, it should also be taken into account here that the pH to be chosen in each case may also depend to a certain extent on the reaction temperature chosen in each case and on the concentration of the 2,4-dichlorobenzoic acid of the formula (2). It may thus be entirely appropriate to work at comparatively low pH values in a large number of cases, in order to suppress the formation of by-products.

In a large number of cases it has proved appropriate to carry out the reaction at a pH of 7.5 to 11, in particular 8 to 10.

The given pH can be maintained particularly easily by adjusting the pH by addition of the base. Since the base employed is consumed in the course of the reaction as a result of neutralization of the hydrochloric acid liberated, the base is usually added to the reaction in an amount such that it is ensured that the pH is maintained.

To establish a constant pH, the alkali can be metered in such that the pH is measured and, if it deviates below the target pH, alkali is added. If the rate of reaction or the alkali consumption as a function of time has been determined by preliminary experiments, a fixed given program for metering of the alkali can also be used on the basis of these results, in order to establish a pH in the desired range.

When the reaction has ended, the N-(2-carboxy-5-chloro-phenyl)glycine of the formula (1) is usually present in the form of an aqueous solution or suspension of its salts. In order to obtain the free N-(2-carboxy-5-chloro-phenyl) glycine, the aqueous solution is acidified by addition of an acid, for example a mineral acid. The free N-(2-carboxy-5-chloro-phenyl)glycine precipitates out of the acidified aqueous solution. It is to be ensured, by addition of a sufficient amount of acid, that the salts of N-(2-carboxy-5-chloro-phenyl)glycines are converted completely into free N-(2-carboxy-5-chloro-phenyl )glycine.

In a large number of cases, it proves sufficient to establish a pH range of 0 to 4, in particular 0 to 2, by addition of the acid. Addition of acid to a pH of −0.5 is possible, but is not desirable in all cases because of the large amounts of acid required.

In order to obtain a readily stirrable suspension, the reaction mixture is advantageously added to the required amount of acid.

The N-(2-carboxy-5-chloro-phenyl)glycine which has precipitated out can be separated off by filtration or extraction, in particular by filtration. Products are usually obtained in a sufficient purity by drying the N-(2-carboxy-5-chlorophenyl)glycine which has been filtered off.

If an even higher purity should be desirable, the N-(2-carboxy-5-chlorophenyl)glycine can be additionally purified by recrystallization or precipitation again from an aqueous solution of its salts.

The process can be carried out under reduced pressure, under normal pressure and under increased pressure. It is particularly suitable for a procedure under normal pressure.

The process can be carried out continuously or discontinuously.

A discontinuous procedure of the process can be carried out particularly easily.

The following examples demonstrate the invention without limiting it.

EXPERIMENTAL PART

EXAMPLE 1

Preparation of N-(2-carboxy-5-chloro-phenyl) glycine in the presence of oxygen and under control of the pH 250 g of water, 1 mol of KOH in the form of 65 g of an 86% strength aqueous solution, 191 g (1 mol) of 2,4-dichlorobenzoic acid, 83 g (1.1 mol) of glycine, 76 g (0.55 mol) of potassium carbonate and 200 mg of copper powder are introduced, while stirring, into a three-necked flask (volume: 1 liter) fitted with a reflux condenser, pH electrode and a pump device with pH control. The apparatus is evacuated and subsequently ventilated with oxygen. The aqueous solution is then heated to the reflux temperature (106° C.) and 50% strength aqueous potassium hydroxide solution is pumped in such that the pH in the aqueous solution is kept at 9. After about three hours, no further potassium hydroxide is consumed, which indicates the end of the reaction.

After acidification to pH 1 and after esterification with diazomethane, the reaction mixture has the following composition, according to analysis by gas chromatography:

| 2,4-Dichlorobenzoic acid* | 1.5% by weight |
| 4-Chlorosalicylic acid* | 6.0% by weight |
| 4-Chlorobenzoic acid* | 1.5% by weight |
| N-(2-Carboxy-5-chloro-phenyl)glycine* | 91.0% by weight |

*as the methyl ester or methoxy compound respectively

EXAMPLE 2

Preparation of N-(2-carboxy-5-chloro-phenyl) glycine in the presence of oxygen and with control of the pH The procedure is as described in Example 1, but instead of 200 mg of copper powder, 350 mg of basic copper carbonate are employed.

After acidification to pH 1 and after esterification with diazomethane, the reaction mixture has the following composition according to analysis by gas chromatography:

| 2,4-Dichlorobenzoic acid* | 1% by weight |
| 4-Chlorosalicylic acid* | 6% by weight |
| 4-Chlorobenzoic acid* | 2% by weight |
| N-(2-Carboxy-5-chloro-phenyl)glycine | 91% by weight |

*as the methyl ester or methoxy compound respectively

Comparison Example 1

Preparation of N-(2-carboxy-5-chloro-phenyl) glycine in the absence of oxygen but with control of the pH 250 g of water, 1 mol of KOH in the form of 65 g of an 86% strength aqueous solution, 191 g (1 mol) of 2,4-dichlorobenzoic acid, 83 g (1.1 mol) of glycine, 76 g (0.55 mol) of potassium carbonate and 200 mg of copper powder are introduced, while stirring at room temperature and as described in Example 1, into a three-necked flask (volume: 1 liter) fitted with a reflux condenser, pH electromode and a pump device with pH control.

The apparatus is degassed by means of ultrasound, evacuated and subsequently ventilated not with oxygen, as stated in Example 1, but with argon.

The aqueous solution which has been freed from oxygen is then heated to the reflux temperature (106° C.) and 50% strength aqueous potassium hydroxide solution is pumped in such that the pH of the aqueous solution is kept at 9.

After three hours, little potassium hydroxide has been consumed, compared with Example 1, and no further potassium hydroxide is consumed, which indicates the end of the reaction.

After acidification to pH 1 and after esterification with diazomethane, the reaction mixture has the following composition, according to analysis by gas chromatography:

| 2,4-Dichlorobenzoic acid* | 87% |
| 4-Chlorosalicylic acid* | 1% |
| 4-Chlorobenzoic acid* | <0.2% |
| N-(2-Carboxy-5-chloro-phenyl)glycine* | 12% |

*as the methyl ester or methoxy compound respectively.

Comparison Example 2

Preparation of N-(2-carboxy-5-chloro-phenyl) glycine in the presence of oxygen, but without control of the pH 250 g of water, 2 mol of KOH in the form of 124 g of a 90% strength aqueous solution, 191 g (1 mol) of 2,4-dichlorobenzoic acid, 75 g (1 mol) of glycine, 76 g (0.55 mol) of potassium carbonate and 200 mg of copper powder are introduced, while stirring at room temperature, into a three-necked flask (volume: 1 liter) fitted with a reflux condenser, pH electrode and a pump device with pH control. The apparatus is evacuated and subsequently ventilated with oxygen.

The aqueous solution is then heated under reflux for 6 hours until the reaction has ended.

After acidification to ph 1 and after esterification with diazomethane, the reaction mixture has the following composition, according to analysis by gas chromatography:

| | |
|---|---|
| 2,4-Dichlorobenzoic acid* | 2% |
| 4-Chlorosalicylic acid* | 13% |
| 4-Chlorobenzoic acid* | 2% |
| N-(2-Carboxy-5-chloro-phenyl)glycine* | 83% |

*as the methyl ester or methoxy compound respectively

We claim:

1. A process for the preparation of N-(2-carboxy-5-chloro-phenyl)glycine, which comprises reacting 2,4-dichlorobenzoic acid with glycine and a base in water at a temperature of 50° to 200° C. in the presence of copper and oxygen at a pH of 7 to 13.

2. The process as claimed in claim 1, wherein 2,4-dichlorobenzoic acid of the formula (2) and glycine are reacted in a molar ratio of 1:1 to 1:2.

3. The process as claimed in claim 1, wherein an oxide, hydroxide, carbonate or bicarbonate of an alkali metal or alkaline earth metal or a mixture thereof is employed as the base.

4. The process as claimed in claim 1, wherein an oxide, hydroxide or carbonate of an alkali metal or a mixture thereof is employed as the base.

5. The process as claimed in claim 1, wherein sodium hydroxide, potassium hydroxide, sodium carbonate or potassium carbonate or a mixture thereof is employed as the base.

6. The process as claimed in claim 1, wherein the reaction is carried out at a temperature of 60° to 160° C.

7. The process as claimed in claim 1, wherein the reaction is carried out at a temperature of 90° to 130° C.

8. The process as claimed in claim 1, wherein metallic copper, a copper(I) or copper(II) compound or a mixture thereof is employed as the copper.

9. The process as claimed in claim 1, wherein a copper(I) salt or a copper(II) salt or a mixture thereof is employed as the copper.

10. The process as claimed in claim 1, wherein 0.005 to 2.5% by weight of copper, based on the 2,4-dichlorobenzoic acid, is employed.

11. The process as claimed in claim 1, wherein 0.05 to 0.5% by weight of copper, based on the 2,4-dichlorobenzoic acid, is employed.

12. The process as claimed in claim 1, wherein the oxygen is introduced as an oxygen-containing gas ranging in oxygen purity up to the level of pure oxygen.

13. The process as claimed in claim 12, wherein the oxygen-containing gas is passed through the reaction mixture during the reaction.

14. The process as claimed in claim 12, wherein air or pure oxygen is employed as the oxygen-containing gas.

15. The process as claimed in claim 1, wherein the reaction is carried out at a pH of 7.5 to 11.

16. The process as claimed in claim 1, wherein the reaction is carried out at a pH of 8 to 10.

17. The process as claimed in claim 1, wherein the pH is adjusted by addition of the base.

18. The process as claimed in claim 1, wherein the process is carried out in an aqueous solution or suspension containing fully or partially dissolved 2,4-dichlorobenzoic acid, glycine and base.

19. The process as claimed in claim 18, wherein the presence of said base results in the formation of a salt of N-(2-carboxy-5-chloro-phenyl)glycine, and said salt, optionally after conversion to an ester or methoxy derivative, is converted to N-(2-carboxy-5-chloro-phenyl)glycine by treatment of the salt, esters or methoxy derivative with an acid, and wherein the final product separated from the thus-treated aqueous solution or suspension is N-(2-carboxy-5-chloro-phenyl)glycine.

20. A process for the preparation of N-(2-carboxy-5-chloro-phenyl)glycine or a salt, ester, or methoxy derivative thereof, which comprises combining 2,4-dichlorobenzoic acid with glycine and a base in an aqueous solution or suspension contained in a reaction zone, at a temperature, of said aqueous solution or suspension, of 50° to 200° C, in the presence of copper, wherein an oxygen-containing gas is introduced into the reaction zone, reacting the 2,4-dichlorobenzene with the glycine, with formation of HCl, and maintaining the pH of the aqueous solution or suspension in the range of 7 to 13 by introduction of additional base.

21. The process as claimed in claim 20, wherein the product of said process is a salt, ester or methoxy derivative of N-(2-carboxy-5-chloro-phenyl)glycine, and said salt, ester, or methoxy derivative is converted to the compound N-(2-carboxy-5-chloro-phenyl)glycine by treatment with acid and is isolated as said compound.

22. The process as claimed in claim 20, wherein the pH is maintained at a level which at least partially suppresses byproduct formation of 4-chlorosalicylic acid.

* * * * *